United States Patent
Tiran et al.

(10) Patent No.: US 9,488,556 B2
(45) Date of Patent: Nov. 8, 2016

(54) CRYOGENIC STORAGE SYSTEM FOR THERMOLABILE SPECIMENS

(71) Applicants: M&R Automation GmbH, Grambach (AT); Medizinische Universität Graz, Graz (AT)

(72) Inventors: Andreas Tiran, Graz (AT); Christian Amon, Kainbach bei Graz (AT); Herbert Ritter, Heiligenkreuz am Waasen (AT)

(73) Assignees: M&R Automation GmbH, Grambach (AT); Medizinische Universität Graz, Graz (AT)

( * ) Notice: Subject to any disclaimer, the term of this patent is extended or adjusted under 35 U.S.C. 154(b) by 116 days.

(21) Appl. No.: 14/400,782

(22) PCT Filed: May 10, 2013

(86) PCT No.: PCT/EP2013/059712
§ 371 (c)(1),
(2) Date: Nov. 12, 2014

(87) PCT Pub. No.: WO2013/171127
PCT Pub. Date: Nov. 21, 2013

(65) Prior Publication Data
US 2015/0121941 A1    May 7, 2015

(30) Foreign Application Priority Data
May 16, 2012 (EP) .................... 12168357

(51) Int. Cl.
*B65D 25/10* (2006.01)
*G01N 1/42* (2006.01)
*F25D 25/00* (2006.01)
*A61B 10/00* (2006.01)
(Continued)

(52) U.S. Cl.
CPC ............ *G01N 1/42* (2013.01); *A01N 1/0268* (2013.01); *A61B 10/0096* (2013.01); *B65D 25/10* (2013.01); *B65D 43/26* (2013.01); *B65D 81/2076* (2013.01); *F25D 25/00* (2013.01)

(58) Field of Classification Search
CPC .. A61B 10/0096; A01N 1/0268; G01N 1/42; B65D 25/10; B65D 25/102; B65D 25/106; B65D 25/108; B65D 81/2076; F25D 25/00; F25D 25/005; F25D 25/04
USPC ...... 53/396, 475, 492, 390; 62/337; 206/443
See application file for complete search history.

(56) References Cited

U.S. PATENT DOCUMENTS 4,771,900 A    9/1988  Leoncavallo et al.
4,898,278 A    2/1990  Leoncavallo et al.
(Continued)

FOREIGN PATENT DOCUMENTS

DE    10 2004 053 170 A1    5/2006
EP    2 237 048 A2           10/2010
WO    WO 98/58215 A1         12/1998

OTHER PUBLICATIONS

International Search Report for PCT/EP2013/059712, published by the International Bureau on Jun. 20, 2013.
(Continued)

*Primary Examiner* — Stephen Castellano
(74) *Attorney, Agent, or Firm* — Knobbe, Martens, Olson & Bear, LLP

(57) ABSTRACT

The invention concerns a storage device (23, 45) for storing receptacles (10), preferably cryo-vials (10), in a carrier structure (3), the storage device (23, 45) comprising pockets (20) each for holding an individual receptacle (10), wherein the pockets (20) are connected one above the other in direction of a common longitudinal axis (59) and the storage device (23, 45) being provided with openings for inserting and retrieving receptacles (10) into and from said pockets (20) in longitudinal direction (60) and/or in lateral direction (61). Also a storage and storage-access system according to the invention is indicated.

17 Claims, 8 Drawing Sheets

(51) Int. Cl.
  *A01N 1/02*  (2006.01)
  *B65D 43/26*  (2006.01)
  *B65D 81/20*  (2006.01)

(56) References Cited

U.S. PATENT DOCUMENTS

| | | |
|---|---|---|
| 5,168,725 A | 12/1992 | Margolin |
| 5,233,844 A | 8/1993 | Knippscheer et al. |
| 5,921,102 A | 7/1999 | Vago |
| 5,964,095 A | 10/1999 | Coelho et al. |
| 2008/0092581 A1 | 4/2008 | Schumann et al. |
| 2009/0144494 A1 | 6/2009 | Lin et al. |
| 2011/0120148 A1 | 5/2011 | Yoshimura et al. |
| 2011/0219788 A1 | 9/2011 | Zimmermann et al. |

OTHER PUBLICATIONS

Written Opinion of the International Search Authority for PCT/EP2013/059712, mailed Jun. 20, 2013.

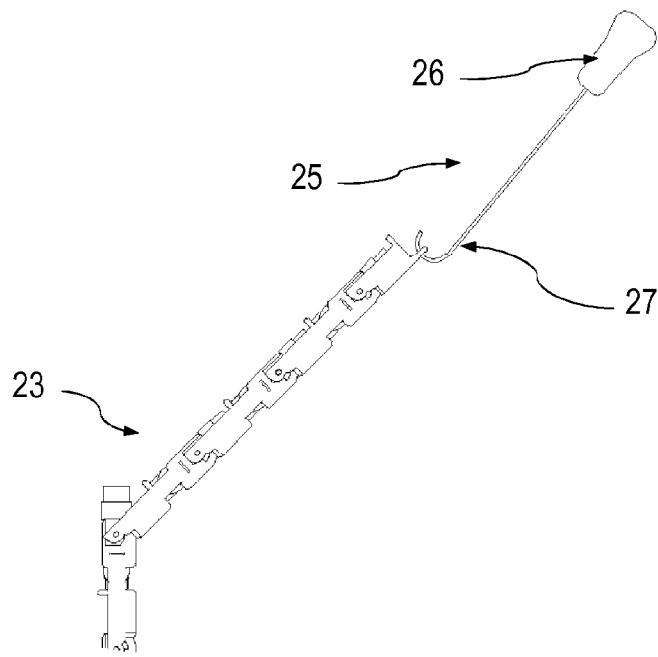
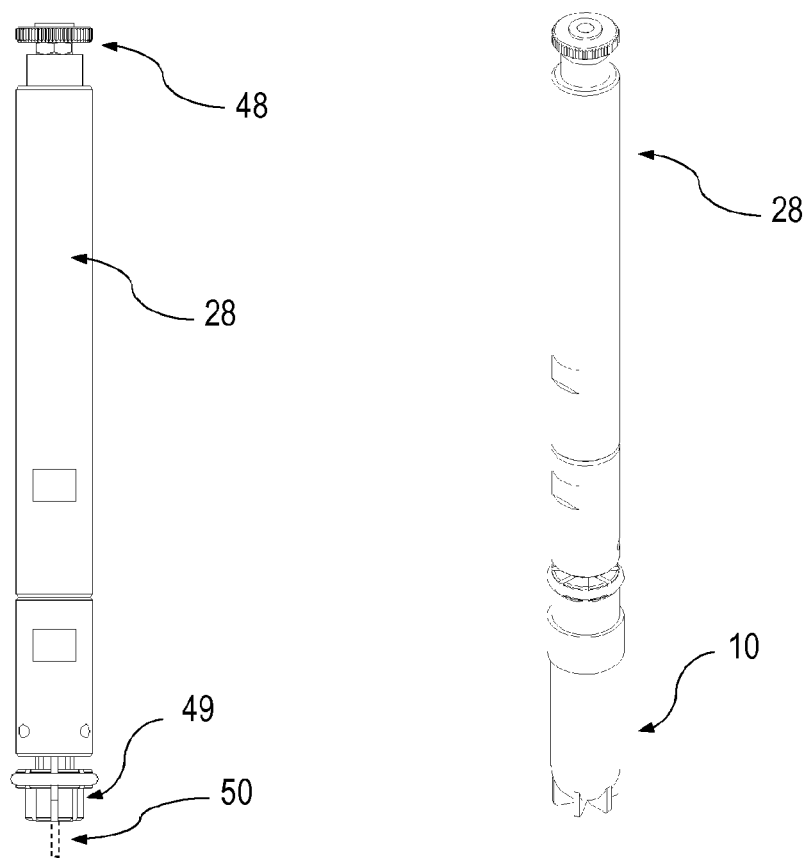
FIG.5
FIG.6A FIG.6B

CRYOGENIC STORAGE SYSTEM FOR THERMOLABILE SPECIMENS

INCORPORATION BY REFERENCE TO RELATED APPLICATIONS

Any and all priority claims identified in the Application Data Sheet, or any correction thereto, are hereby incorporated by reference under 37 CFR 1.57. This application is the national phase under 35 U.S.C. §371 of prior PCT International Application No. PCT/EP2013/059712 which has an International Filing Date of May 10, 2013, which designates the United States of America, and which claims priority to European Application No. EP 12168357.7 filed May 16, 2012. Each of the aforementioned applications is incorporated by reference herein in its entirety, and each is hereby expressly made a part of this specification.

The present invention relates to storage devices for storing receptacles, preferably cryo-vials, in a carrier structure, the storage device comprising pockets each for holding an individual receptacle. Furthermore the present invention relates to a storage and storage-access system comprising said storage devices.

The present invention relates to a new storage and storage-access system, in which a plurality of samples are organized in a vertically accessible form that allow for insertion or retrieval of samples one at a time or in multiples, either manually or automatically. More particularly, this invention relates to a storage and storage-access system including a light-emitting guiding system for quick and accurate insertion and retrieval of samples into or from a storage container featuring the access opening on the top. More specifically, this invention relates to a storage and storage-access system for the preservation of thermolabile samples or products at various temperatures, including but not limited to the temperature of liquid nitrogen.

Thermolabile samples such as but not limited to blood, cells, cerebrospinal fluid, tissues or other biological materials and thermolabile products such as but not limited to synthesized peptides or chemical compounds require stable and defined temperatures especially for long-time storage. There is increasing evidence that such samples and products are very sensitive to temperature changes even far below thawing temperature and to mechanical shocks because of their brittleness at very low temperatures.

Many conventional cryogenic storage systems for open-lid tanks consist of simple racks having multiple shelves. Documents U.S. Pat. No. 4,771,900 and U.S. Pat. No. 4,898,278 show storage systems where storage boxes each storing a plurality of specimens are stacked up in shelves. U.S. Pat. No. 5,168,725 proposes a similar system for cryogenically stored fluid packets such as blood. At these storage systems, whole racks holding several storage boxes have to be removed from storage containers. Afterwards the storage boxes have to be removed from racks and opened to insert or retrieve individual samples, altogether a slow and tedious operation when performed by a single person and with proper personal protection gear. Even a bigger problem is the fact that at every insertion and retrieval action of a single sample many other samples that are stored within the same rack to be removed as well as in neighbouring racks within the storage container are affected.

Disadvantageously every manipulation of a single sample causes repeated and considerable temperature changes and mechanical shocks to a large number of samples, resulting in a decrease in quality and integrity of these samples. Moreover, upon repeated sample manipulation with storage and access actions, humidity of the ambient atmosphere will immediately condensate on the cold surfaces of a removed rack. As a result, labelling of specimens is concealed by condensation, and accuracy and speed of storage and access operations are greatly affected.

Several automated cryogenic storage devices have been disclosed. Some of them are specifically applicable to storage of larger cartridges such as those proposed for blood or stem cell products, such as shown in US 2009/0144494 and U.S. Pat. No. 5,964,095.

Other developments such those presented in U.S. Pat. No. 5,233,844, U.S. Pat. No. 5,921,102 or US 2011/0219788 focus on small volume samples commonly stored in cryo-vials. All of them suffer from the disadvantage of having many moving parts and being slow in their operation. Moreover, all of them have very high investment and operating costs. Therefore, the vast majority of cryogenic storage systems used in medicine, research, and forensics are still not automated and insertion and retrieval of samples are mainly performed manually despite of the serious, unavoidable quality problems listed above. An improved system has been disclosed recently in US 2008/0092581 A1, however handling of the system is cumbersome and time consuming. Due to the fact that a considerable part of the precious space within the storage container has to be provided as moving space or working area the degree of space utilisation within a given storage container is weak. Thus a need exists for an efficient and affordable storage and storage-access system that guarantees quick and easy placing and retrieval of samples while keeping all other samples at optimal storage conditions, both in manual and automated operation.

Thus an object of the present invention is to provide an improved storage and storage-access system wherein thermolabile samples or products may be stored or retrieved one at a time or in multiples, either manually or automatically.

Another, more specific, object of the present invention is to provide a cryogenic storage and storage-access system wherein all specimens are stored at essentially the same low temperature, regardless of the location of specimens in a system and regardless of ongoing insertion and retrieval operations.

A further object of the present invention is to provide a storage and storage-access system which has greatly reduced insertion and retrieval times and which can be operated easily by a single person without the need of lifting heavy containers or performing cumbersome operations. A streamlined operating procedure and tools supporting all steps have to guarantee temperature constancy and quality of samples.

Another object of the present invention is to provide a storage and storage-access system which supports storage and retrieval actions by an intuitive guiding system to quickly and accurately access the correct storage position and/or sample and to prevent handling mistakes.

Another object of the present invention is to provide a storage and storage-access system with means for efficiently and quickly removing of all stored specimen from a storage container in case of a storage container malfunction.

Another, more specific, object of the present invention is to provide a storage and storage-access system which minimizes fog formation upon opening of the lid and wherein the formation of ice crystals on stored receptacles is substantially reduced if not eliminated.

Another, more general, object of the present invention is to provide a storage and storage-access system with minimized operating costs. The main reason for high operating costs is loss of temperature and waste of energy at access and retrieval processes. These processes have been optimized so that they can be performed very quickly without the need to remove whole racks from a storage container and to expose them to ambient air temperature. Thus, short opening times of a storage container and high storage density allow to reduce storage costs per specimen to a minimum.

The afore-mentioned tasks and objects are solved within the present invention by providing a storage device according to the preamble of claim 1 with the features of the characterising part of claim 1. Other advantageous embodiments of the invention are presented in the dependent claims.

At a storage device according to the invention for storing receptacles, preferably cryo-vials, in a carrier structure, the storage device comprising pockets each for holding an individual receptacle, wherein the pockets are connected one above the other in direction of a common longitudinal axis and the storage device being provided with openings for inserting and retrieving receptacles into and from said pockets in longitudinal direction and/or in lateral direction. A storage device can have a rod-like shape if its structure is rigid. Alternatively a storage device can have a chain-like shape if its structure is flexible or bendable.

Particularly advantageous for a storage device according to the invention further comprising interconnected elements is that each element arranged one above the other comprises one pocket for holding an individual receptacle.

In a practical variety of the inventive storage device each pocket is concentrically arranged with the longitudinal axis, whereby a cross-sectional perimeter of the pocket is larger than a cross-sectional perimeter of the receptacle. The invention is not limited to store receptacles like cryo-vials that are usually cylindrical. Also receptacles with a polygonal base area can be stored in respective storage devices.

Usefully at a storage device according to the invention each pocket comprises at least one holding device like a bottom holding device preventing each receptacle from falling out of the storage device.

In a preferred realisation of the invention the elements of a storage device are pivotably interconnected with its adjacent elements so that they are pivotable by a pivot angle in relation to the longitudinal axis. Thus the elements of the storage device are interconnected with each other like chain links.

In a preferred embodiment of the invention each pocket of a storage device is accessible for insertion or removal of receptacles in longitudinal direction from above when the upwardly adjacent element is pivoted from the longitudinal axis by a pivot angle.

Advantageously each element of an inventive storage device comprises a retaining mechanism securing neighbouring elements in dedicated positions, either in a rod-like position in direction of the longitudinal axis or in a pivoted position hinged by a pivot angle.

In another preferred embodiment of the invention each storage device and/or each pocket has an individual identification marking.

Particularly convenient is a storage device according to the invention which comprises on its top side of the storage device an eye matching with a hook of an auxiliary tool. Thus it is very comfortable to catch a targeted storage device with a matching hook-like tool.

Within the scope of the invention a storage and storage-access system comprises:
at least one storage device for storage of receptacles,
a storage container having an interior and an open top,
a carrier structure mounted in the interior of the storage container providing a framework to store a plurality of storage devices in parallel in a vertical order,
said carrier structure providing access openings on the top for enabling insertion and retrieval of receptacles stored in storage devices from above and, oppositely, a closed side at the bottom of the carrier structure to prevent the storage devices from falling out when the carrier structure is lifted.

A storage and storage-access system in accordance with the present invention comprises a carrier structure that may be introduced into open lid storage containers. A storage container is for example cylindrical with a round base area and an opening on its round upper side for loading and unloading samples. Preferably, the carrier structure may be subdivided into individual units which may be embodied as rack towers as shown in the drawings, but may also have any other suitable form. The carrier structure serves to store a plurality of specimen containing receptacles of similar shape and size in a vertical order. Preferably, the carrier structure for round shaped receptacles such as cryo-vials may be realized as a long-stretched, vertically oriented honeycomb structure so as to optimize packing density while lowering manufacturing costs and reducing manufacturing processing. However, the carrier structure may also be realized in any other conceivable construction suitable to keep specimen containing receptacles in a vertical storage order. For receptacles that are not round, the geometry of the inner framework of the carrier structure may deviate from a hexagonal honeycomb geometry in order to maximize packing density. The carrier structure is provided with access openings on the top for enabling insertion and retrieval of specimen containing receptacles from above and, oppositely, a closed side at the bottom. The closed side of the carrier structure prevent receptacles from falling out when the carrier structure is lifted.

Advantageously a carrier structure according to the invention provides:
vertical storing of storage devices each holding receptacles in an certain order;
access of each storage device from the top of the carrier structure;
minimum amount of receptacles manipulated at a storage and retrieval process;
ergonomic process operation for service personnel;
compatibility with existing storage or rack systems;
fast evacuation capability;
fast atmospheric adjustment.

Pursuant to another feature of the present invention, specimen containing receptacles within the carrier structure may advantageously be disposed on a long, rod-shaped storage device in order to insert receptacles into the carrier structure or retrieve them from it. Preferably, a storage device may be assembled from individual elements each providing a pocket for holding individual receptacles. In the present invention, elements may be interconnected by hinges, so that pivoting a storage device between two links renders a pocket in a lower element accessible for insertion or removal of a receptacle, whereas straightening of a storage device locks receptacles into position within a device.

According to the present invention, a storage device is suggested to be lifted out of the carrier structure exactly to the height of the element that is targeted for insertion or retrieval of a receptacle. Upon pivoting the upper part of a storage device, the storage position is freed for immediate, direct access. A hook type auxiliary tool can assist at a storage device manipulation process. After insertion or retrieval of a receptacle, a storage device may be straightened and returned back into the carrier structure again. The whole procedure takes only a few seconds and may be easily performed by a single person. Due to a retaining feature provided by the links in a straight, non pivoted storage device the receptacles can be located in the pocket of the elements with some axial play without the risk of falling out. Therefore an effortless insertion and removal of receptacles from a pivoted storage device is ensured.

Pursuant to the present invention, elements may be designed so as to fit all commercially available cryo-vials, but they may be adapted easily to fit all other formats of specimen containing receptacles. Elements can be curved at edges so as to facilitate smooth insertion into and retrieval from the carrier structure.

Further, carrier units of the carrier structure, according to the present invention, can be packed within a storage container to a very high density, so as to have actually no gaps between individual carrier units of the carrier structure. This is possible as those carrier units are always held in place without any need to remove them unless there is a need for evacuation of a whole storage container. The tops of the carrier units of the carrier structure and the storage devices together form a closed top surface which prevents temperature loss or invasion of foreign matter such as accidentally dropped receptacles. In addition, the closed top surface efficiently prevents condensation of surface moisture on stored receptacles, so that identification labels on receptacles remain easily readable and operators can carry out the insertion and retrieval process quickly and accurately.

A storage and storage-access system according to the present invention may further comprise a light-emitting guiding system in order to enhance speed and accuracy to retrieve the correct storage or retrieval position. A light-emitting guiding system consists of a control unit such as a computer to implement insertion and retrieval operations as well as tracking of stored specimen. A control unit is operatively connected to a light-emitting head that may be affixed nearby a storage container in order to project customised display options on the surface of the carrier structure. After correct adjustment of the light-emitting guiding system with respect to the carrier structure within a container, the selection of a certain storage position by marking the targeted storage device by a projected light marking like a cross-hair and additionally by indicating the position of a targeted element in a storage device by alphanumeric codes is both supportive and confusion avoiding.

In another advantageous embodiment of the invention the storage and storage-access system can comprise a barcode reader in order to unambiguously identify markings of receptacles being inserted to or removed from said storage and storage-access system. The barcode reader can be operatively connected to a control unit to identify certain receptacles. A light-emitting guiding system can indicate the location of specimens that have either been selected by manual data entry or by a scanning process or by an order that has been placed by a commanding control system. A control unit can either have its own database that keeps track of an individual element pocket status or this logic can also be a slave to a master data base.

Integrating all of the aforementioned features of the present invention into an optimized process, a method for manually storing or retrieving a plurality of receptacles with a storage and storage access system comprises the following steps:

generating an insertion order or retrieval order at the control unit of the storage and storage-access system to assign a specified storage position to a receptacle to be stored or retrieved, scanning of barcode on the receptacle to positively identify the handled specimen in case of insertion into the storage system identifying the specified storage position of the receptacle including a marking of a pocket of a targeted storage element in a storage device and, if applicable, a rack marking of a targeted carrier structure unit by projecting an individual identification marking directly onto the top surface of the carrier structure by means of the light-emitting guiding system, pulling out the identified storage device to the height of the targeted element, pivoting the storing device, for an insertion order placing said receptacle in the targeted pocket of said element, or alternatively for a retrieval order retrieving said receptacle out of the targeted pocket of said element, sliding back said storage device into the carrier structure and scanning of barcode on the receptacle to positively identify the handled specimen in case of removal from the storage system.

Pursuant of a specific feature of the present invention, the individual carrier units of the carrier structure may be provided with shackles at the top so that the entire carrier unit with all storage devices and specimen containing receptacles may be removed easily and quickly from a storage container in case of malfunction.

Pursuant of a specific feature of the present invention, the carrier units of the carrier structure may be designed in the same outside geometry like other commercially available rack type systems in order to be used in combination or to gradually replace existing commercially available systems.

Pursuant to yet another specific feature of the present invention, an opening mechanism of the lid of a cryogenic storage container may be provided with a speed controlled lifting mechanism in order to minimize fog and ice formation. Fast lifting of a lid causes air turbulences and fog formation by swirling of humid air with cold nitrogen gas. Speed controlled lifting of a lid efficiently minimizes air turbulences in a storage container and efficiently prevents impairment of visibility and icing of racks and receptacles, both of them unwanted and detrimental effects.

Since a storage and storage-access system according to the present invention can be manipulated manually, system shut down due to electrical power failure or robotic fault can be avoided. The mechanism is simple and resulting in low manufacturing costs. Also hook-up and start-up requirements including start-up-time and infrastructure can be kept at a minimum. Operator training, operator familiarization as well as maintenance are negligible in comparison to complex automated systems. Further, for an insertion and retrieval process only a very small opening in the covering surface of the carrier structure is required. Thus insertion and retrieval of a single receptacle like a cryo-vial can be performed so quickly, that temperature fluctuations in not to be accessed specimen can be kept to a extremely low level, even for specimen located in the very storage device that is lifted out of the carrier structure. The number of physically moved specimen at a single access event is reduced to the samples within the single storage device to manipulate. Lifting and replacing movement of a storage device is a very quick and smooth action. Thus, loss of quality or integrity of specimens due to abrupt temperature change and/or mechanical shocks can be avoided. Where a storage container is a cryogenic storage apparatus, the consumption of liquid nitrogen may be greatly reduced due to a minimal temperature loss upon insertion and retrieval processes.

Thus a storage and storage-access system according to the invention has at least the following advantages compared to conventional storage devices:
- storage and retrieval of receptacles with faster process operation;
- receptacles are stored in more stable environment with less temperature fluctuation and less mechanical shocks;
- storage with less energy consumption;
- storage and retrieval with higher reliability due to prevention of mix up of samples;
- storage and retrieval with increased safety for operating personnel or user.

Other objects, advantages, and novel features of the present invention will become more apparent from the following detailed description when taken in conjunction with the accompanying drawings:

FIG. 5 is a front view illustrating the use of an example of an auxiliary tool to lift and pivot a storage device to access receptacles from the top;

FIG. 6A is a front view of a preferred embodiment of a vial gripper for easy and secure manipulation of cryo-vials by hand;

FIG. 6B is an isometric view of a preferred embodiment of a vial gripper with a clamped vial attached thereto;

Figure 7A:
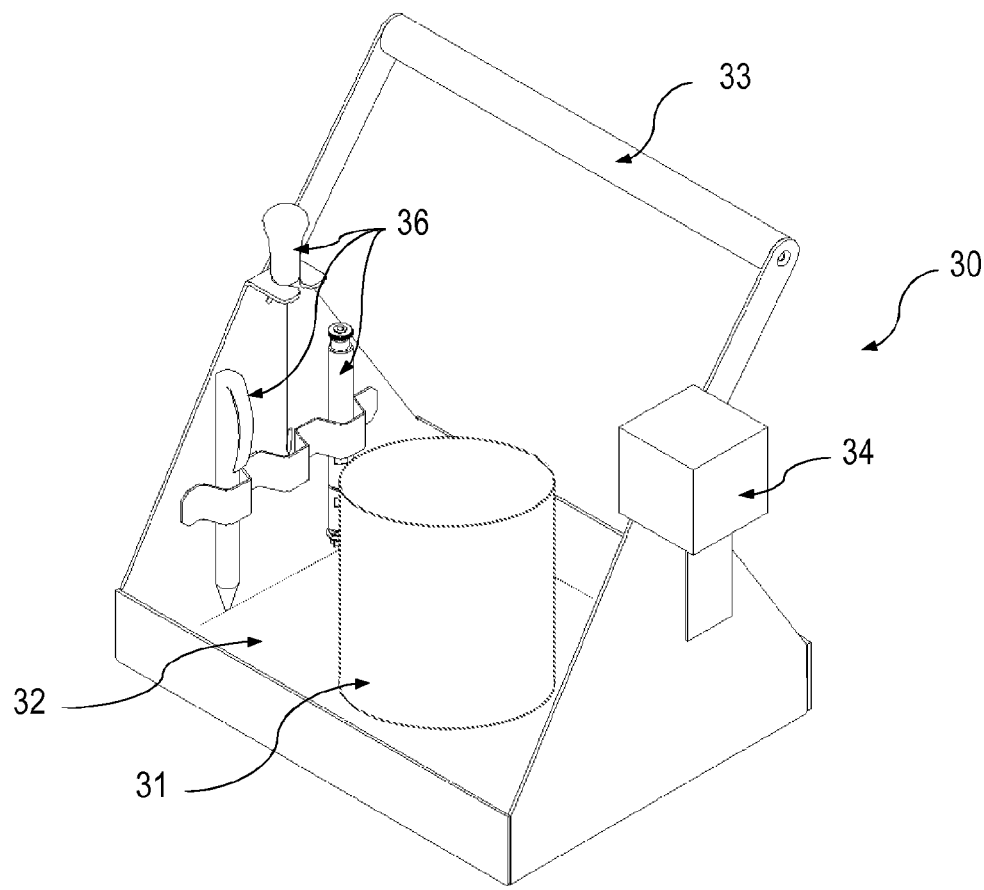
FIG. 7A is an isometric view of a preferred embodiment of a sample and tool holder that assists at a receptacle storing and retrieval process.
Figure 7B:
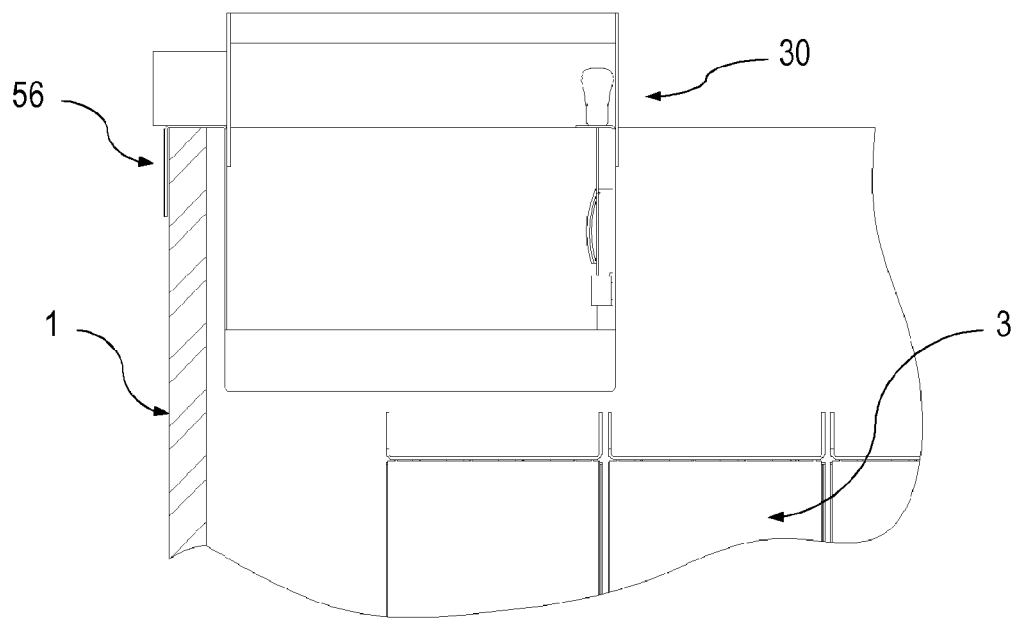
Figure 8A:
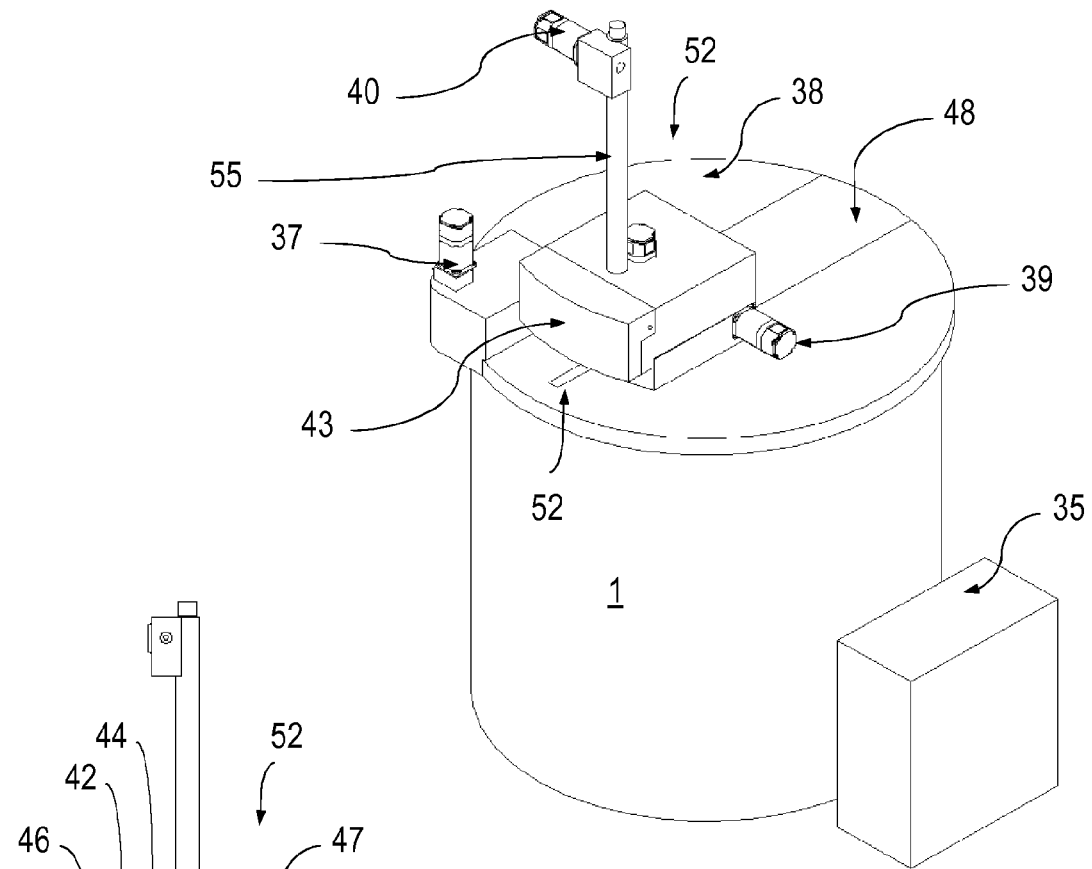
Figure 8B:
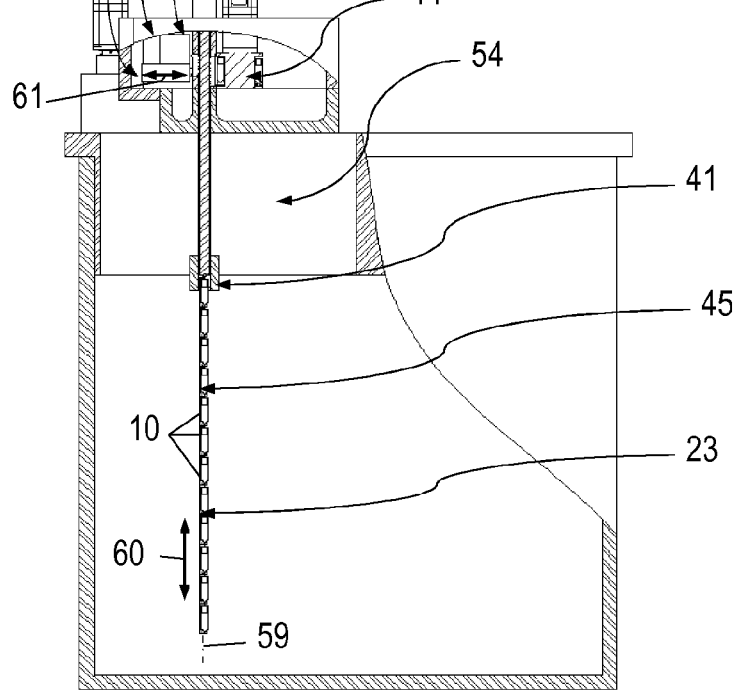
Figure 9A:
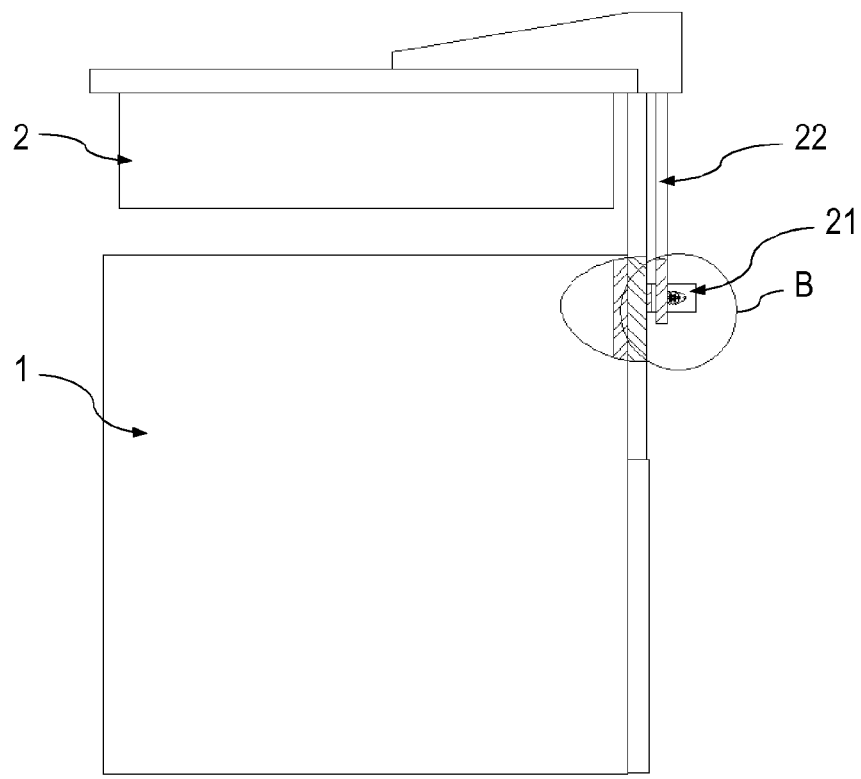
Figure 9B:
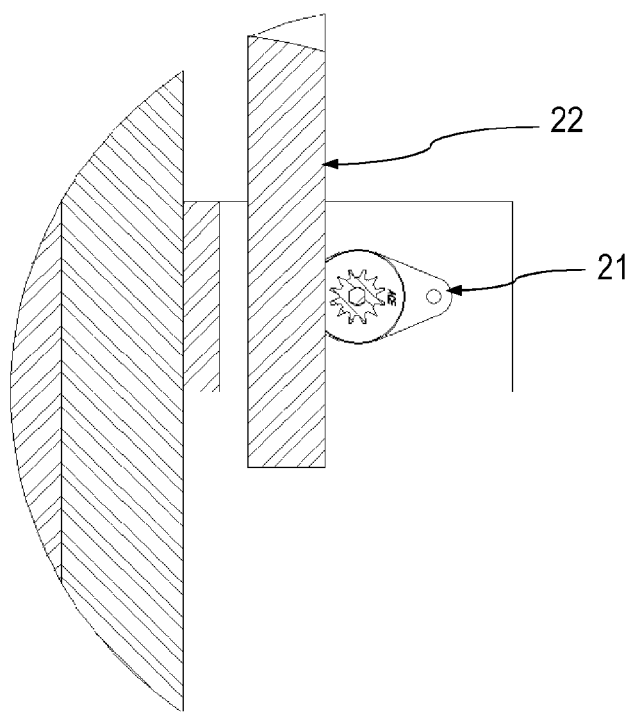

FIG. 7B a sectional view illustrating placing of a sample and tool holder on a rim of a storage container;

FIG. 8A is an isometric view of a preferred embodiment of an automatic version of the present invention;

FIG. 8B is a cut out of a sectional view along a vertical plane illustrating a preferred embodiment of an automated version of a storage and storage-access system according to the present invention with a rotatable, slit top cover, an lift mechanism for storage devices and a cryo-vial handling device;

FIG. 9A is an elevational view of a preferred embodiment of a speed controlled cover lift mechanism at a half way open cover position;

FIG. 9B is a detail cross section of a preferred speed controlled cover lifting mechanism embodiment.

Figure 1A:
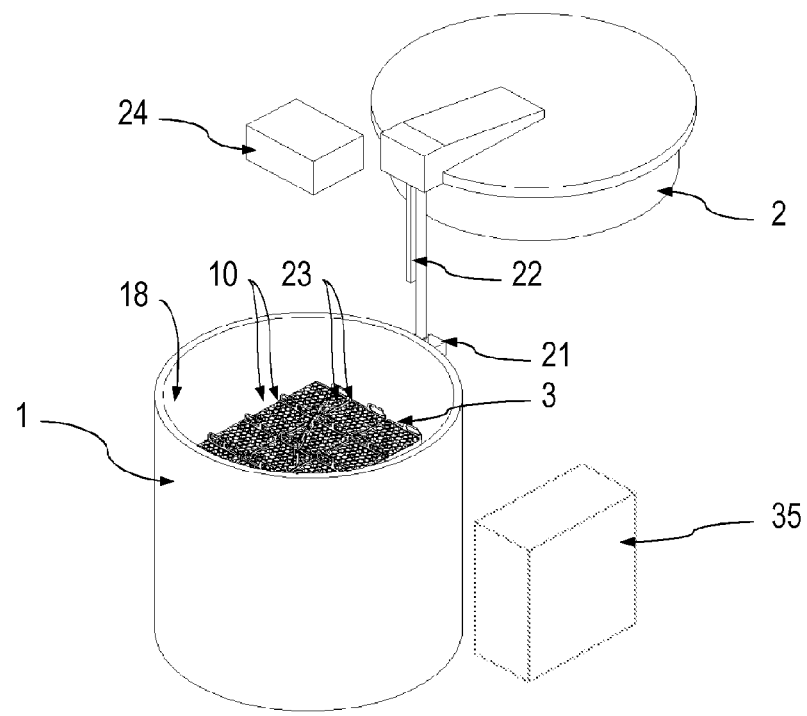
FIG. 1A is an isometric view illustrating a preferred embodiment of the present invention.
Figures 1B, 1C:
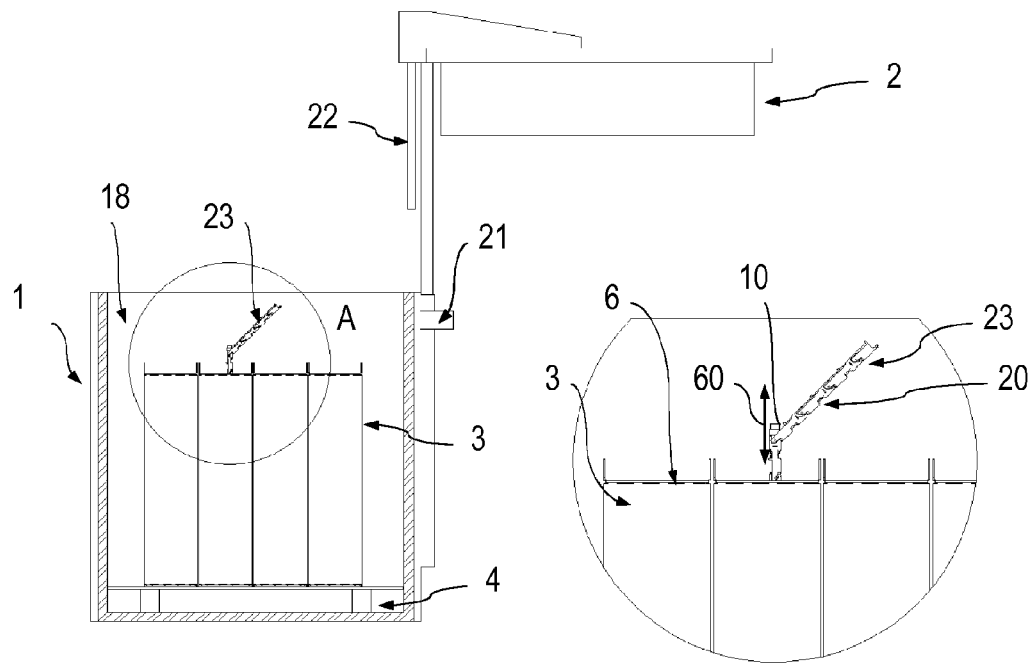
FIG. 1B is a sectional view along a vertical plane illustrating a preferred embodiment of a storage and storage-access system according to the present invention within a conventional storage container.
FIG. 1C is a detail view illustrating a preferred embodiment of the carrier structure with a partially raised storage device that is pivoted for removal of a receptacle.

With reference to FIG. 1A and FIG. 1B, a cryogenic storage container 1 is shown defining an interior 18 adapted to contain thermo labile samples or products. Any conventional means (not shown) such as liquid nitrogen is utilized to maintain the interior 18 of the container 1 at cryogenic temperatures. In essence this cryogenic storage container 1 is preferably a commercially available product, commonly used to store receptacles 10 containing thermo labile specimens. Particularly, a storage and storage-access system according to the present invention requires an open lid storage container 1 where access from the top is granted. An insulating cover 2 of a storage container 1 can be equipped with an opening mechanism such as but not limited to lift-, tilt-, pivot- and/or lift-slide-mechanisms.

With reference to FIG. 9A, a preferred embodiment of a speed controlled cover lifting mechanism to lift an insulating cover 2 of a cryogenic storage container 1 is shown which can be added to commercially available systems. A speed controlled cover lifting mechanism must ensure that a certain cover lifting speed within a certain cover lifting range is not exceeded.

Different solutions are possible and a preferred embodiment is shown in FIG. 9B which shows in detail the area B indicated in FIG. 9A. In FIG. 9B a rotary damper 21 in combination with a gear rack 22 is shown. At a certain cover lifting height the speed must no longer be controlled because the cover lifting speed no longer generates air turbulences and its negative side effects in a storage container. At the maximum top cover lifting stroke gear racks are no longer engaged with rotary dampers. A horizontal rotation of the insulating cover is therefore possible. Re-engaging of gear rack 22 with rotary damper 21 is no problem due to the fact that a guiding mechanism prevents rotary motion of the insulating cover at lower lifting height. Because cover lifting opening speed is slowed down only within a certain cover lifting stroke an opening process is not significantly delayed. The manual closing force and speed is not affected because a rotary damper 21 is only effective in one direction of rotation.

Figure 3:
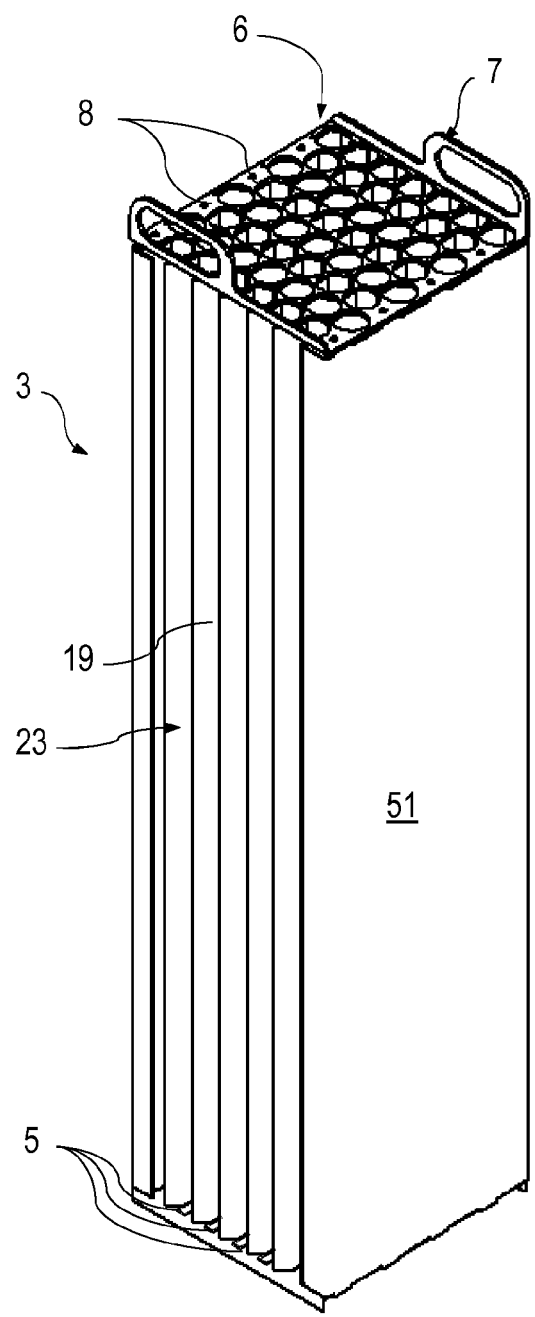
FIG. 3 is an isometric view of a preferred embodiment of a carrier unit of the carrier structure, respectively a rack tower.
Figure 4A:
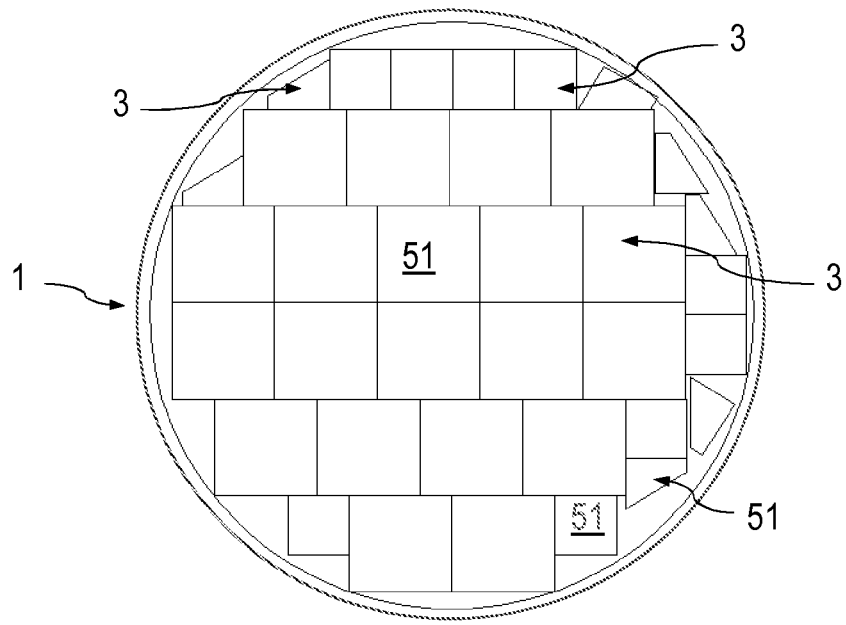
FIG. 4A is a top view illustrating a preferred embodiment of a carrier structure built up of an array of rack towers in a storage container to maximize packing density and also illustrates three different versions of carrier structure units each with different geometries of basis area.

As best shown in FIG. 1A and FIG. 1B, a carrier structure 3 is mounted in the interior 18 of the storage container 1. The carrier structure 3 can be placed directly on the bottom of the storage container 1 or be placed above the ground for example on an intermediate platform 4. The carrier structure 3 according to this invention can have different heights to fit an available height in a storage container 1. For practical reasons, the carrier structure 3 might be divided into smaller, discrete carrier units. A preferred embodiment of such a carrier unit is a rack tower 51 made in accordance with the present invention as shown in FIG. 3. However, a carrier structure 3 and/or a discrete carrier unit thereof like a rack tower 51 can assume any conceivable outer form in order to maximise utilization of space within the interior 18 of the storage container 1 and to match best with the shape of the receptacles 10. Moreover, size and shape of a rack tower 51 of the present invention can have similar outside geometry of conventional rack systems on the market. In this way, a combined usage of commercially available rack systems together with rack towers 51 according to the present invention within the same storage container is possible. Usually, cryogenic storage containers 1 have a cylindrical shape. Referring to FIG. 4A, carrier structures 3 and rack towers 51, respectively, in accordance with the present invention with different footprint can maximize storage capacity and therefore utilize an available space in a storage container 1 more effectively. FIG. 4A shows examples of storage racks 51 with different footprints.

A rack tower 51 as shown in FIG. 3 is the preferred embodiment of an individual carrier unit of the carrier structure 3 according to the present invention. Rack towers 51 locate storage devices 23 designed for manual operation and/or storage devices 45 designed for automated operation and make them randomly accessible from top surface 6 by lifting them vertically upwards in longitudinal direction 60 as depicted in FIG. 1C. The top surface 6 of a rack tower 51 can also have a marking 8 included for identification purposes. Shackles 7 at the top of the rack tower 51 allow for ergonomic manipulation of rack towers 51 such as fast and secure evacuation out of a malfunctioning storage container 1.

Figures 2A, 2B:
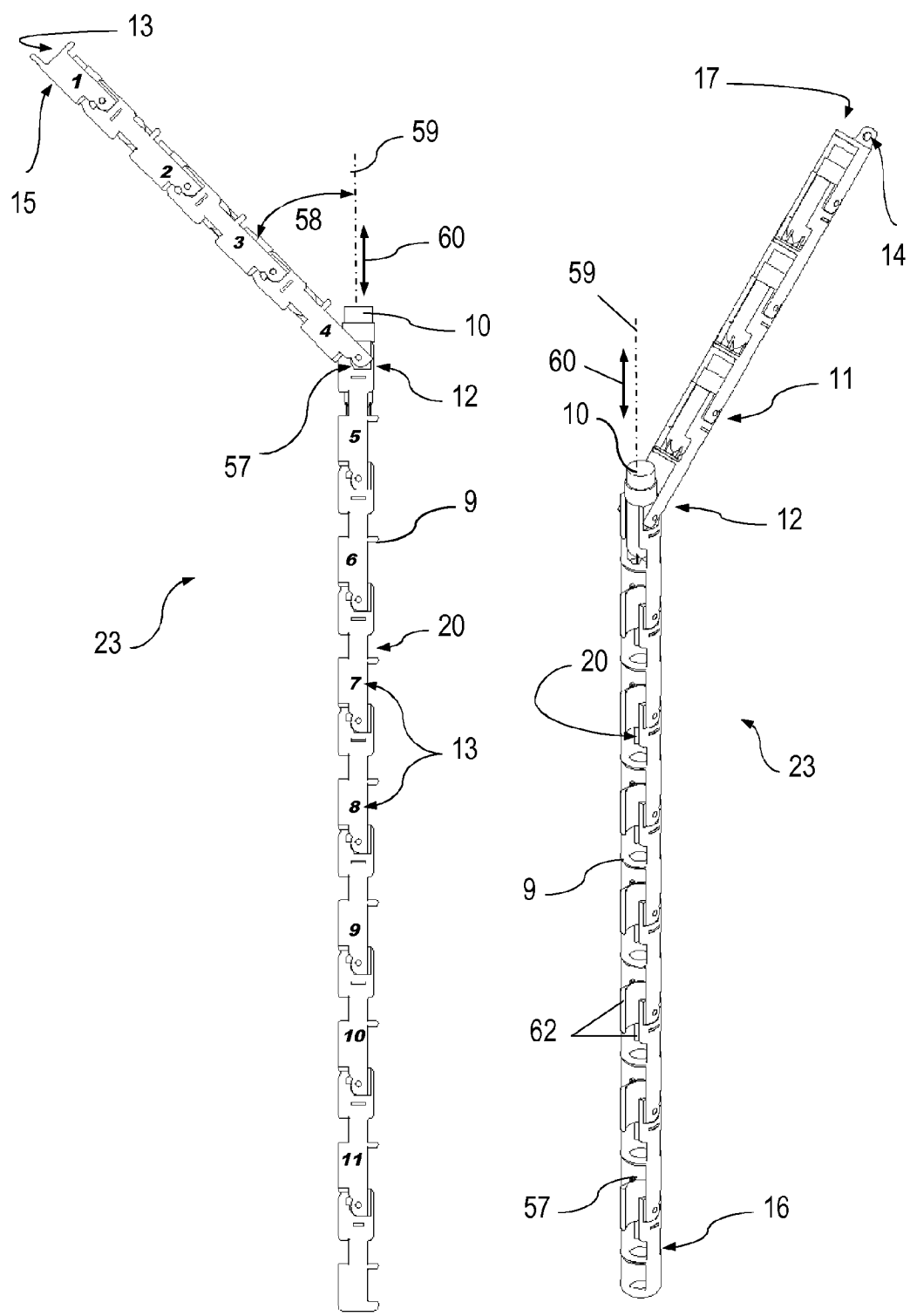
FIG. 2A is front view illustrating a preferred embodiment of a storage device that is pivoted for removal of a cryo-vial shaped receptacle held in the pocket of an element.
FIG. 2B is an isometric view of the storage device as shown in FIG. 2A.

Storage devices 23 as depicted in FIG. 2A are guided individually within a rack tower 51, for example by corrugated metal sheets 19, as indicated in FIG. 3. Therefore not all storage spots within a rack tower 51 must be filled with storage devices 23 at all times. A rack tower 51 may contain several openings 5 in its sidewalls, in its bottom surface, etc. to ensure unobstructed gas flow and to reduce the weight of the rack tower 51.

The worldwide most commonly used form of receptacles 10 to store small samples are cryo-vials 10. Therefore, presented storage devices 23 are optimized to receive cryo-vials 10. However, storage devices 23 may also be realized in any other conceivable construction suitable to keep receptacles 10 of other forms. The preferred embodiment of a storage device 23 according to the present invention as shown in FIG. 2A and FIG. 2B consists of several elements 11. The length of a storage device 23 is determined by the amount of elements 11 used. Each element 11 provides a pocket 20 to receive and hold a cryo-vial 10. When a storage device 23 is kept straight, cryo-vials 10 are locked in the pockets 20 and due to a bottom holding device 9 are prevented from falling out. Cryo-vials 10 can be removed or placed easily in an element 11 in vertical direction 60 when an upper part of a storage device 23 is pivoted out of the way as shown in FIG. 2A. Thus, holding devices 62 are required to prevent unintended loss of the receptacles 10 when the storage device 23 is taken out of a carrier structure 3. Subject to the application receptacles 10 can also be removed or placed in pockets 20 in a lateral direction 61 in a rod-like shaped storage device 45 designed for automated operation. Holding devices are not required in a storage device 45 as receptacles are kept in place by the corrugated metal sheets within the carrier structure or by the isolated tube 55 during the insertion and removal process.

The size of a pocket 20 may provide an axial play around a cryo-vial 10 in an element 11 to allow for easy placing and removal in and out of a pocket 20. When elements 11 are pivoted back a retaining mechanism 57 can restrict a pivot angle 58. Also when elements 11 are kept straight the retaining mechanism 57 retain elements 11 in a straight position. These two mentioned retaining features guarantee better handling and eliminate elements 11 pivoting freely around. With this feature it is possible to specifically pivot neighbouring elements 11 at any targeted pivot point 12.

Preferably, a storage device 23 consists of a top element 15, a free definable amount of middle element 11 and a bottom element 16.

A top element 15 has a small eye 14 on its top side 17 that allows to pick a targeted storage device 23 with an auxiliary hook type tool 25 as shown in FIG. 5 and lift the specified storage device 23 out of a rack tower 51. A top link 15 can also include a marking 13 for visible identification from the top side 17. Middle links 11 can also include markings 13 that allow for quick identification or provide assistance at manipulation processes. A bottom link 16 can be designed longer to ensure better guidance in rack towers 51 when accessing the lowest storage position in a device or simply act as a spacer for a best height in a rack tower 51. Top links 15 are ideally plane with the top surface 6 of the rack tower 51 when in storage position to minimize temperature loss towards the top when a storage container 1 is opened. Thus the top link 15 works as insulation cover for the receptacles 10 stored within each storage device 23. All edges of elements 11, 15, 16 may be curved to allow for smooth insertion into a rack tower 51.

Figure 2C:
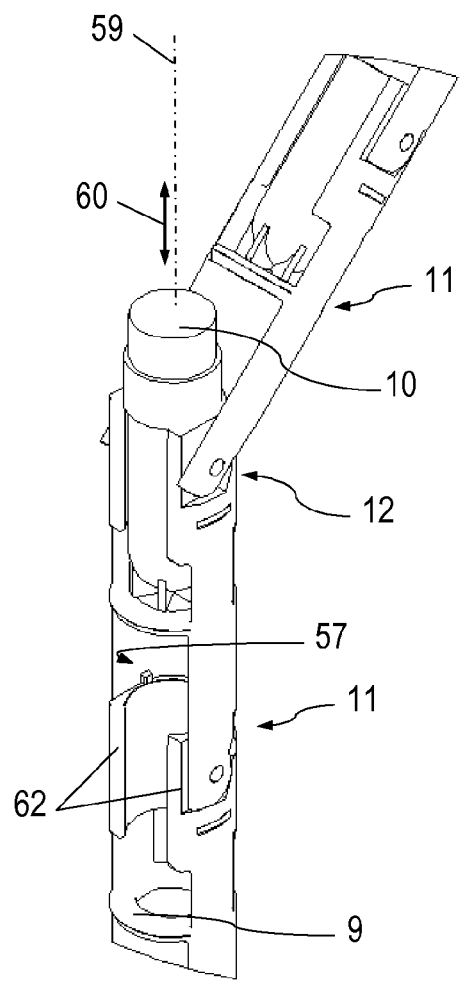
FIG. 2C is an enlarged view of a pivoted element as shown in FIG. 2B.

According to the present invention, a storage device 23 is suggested to be lifted out of a rack tower 51 exactly to the height of the element 11 that is targeted for insertion or retrieval of a certain cryo-vial 10. Upon pivoting the upper part of the storage device 23 as shown in FIG. 2A and in more detail in FIG. 2C, a certain storage position is freed for immediate, direct access of the particular receptacle 10.

Figure 4B:
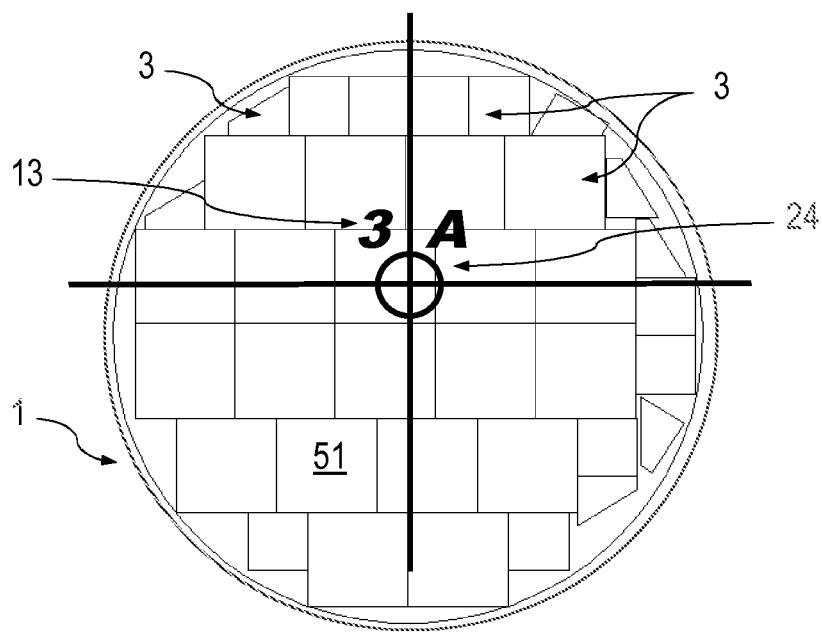
FIG. 4B is a top view of an example of indication of a retrieval position by a light-emitting source.

A light-emitting guiding system 24 as shown in FIG. 1A can be supportive when working with cryogenic storage containers 1. In case ice and fog blur the sight when the insulating cover 2 of the storage container 1 is opened it can be difficult to navigate within the interior 18 of the storage container 1 to find a storage position of a particular receptacle 10. A light-emitting guiding system 24 can for example help at the arrangement of carrier structures 3 in a storage container 1 or indicate desired specimen locations in a storage container 1 as shown in FIG. 4B. The guiding system 24 speeds up the working progress and increases process accuracy and hit ratio, respectively. The working range of light-emitting guiding systems 24 is flexible. Mounting of the guiding system 24 on a ceilings or frame structures is therefore an option. Light-emitting sources can be based on a laser technology or projector technology to project the respective position markings 13 of the particular receptacle 10 on the top surface 6 of the carrier structure 3 or rack tower 51, respectively.

Storage containers 1 that maintain a temperature at or near the temperature of liquid nitrogen require operators to wear special protection gear and make handling of receptacles 10 and storage devices difficult. Properly designed support tools 25 make the operation process saver and more convenient. A hook type auxiliary tool 25 as shown in FIG. 5 can assist at a storage device 23 manipulation process. Preferably, it consists of a knob 26 for better grip and a hook shaped wire 27 that allows a secure connection with the small eye 14 at the top link 15 of the storage device 23 during manipulation of it. A wire shape also reduces the risk of overstressing elements during handling.

A vial gripper 28 as shown in FIG. 6A reflects a preferred embodiment to securely and conveniently manipulate cryo-vials 10. Triggering the mechanism of a vial gripper 28 allows grabbing of cryo-vials 10, which can be seen in FIG. 6B. The preferred embodiment exists of a knob located on the top of a vial gripper as trigger 48. This trigger 48 can be actuated easily by a thumb with or without gloves. The trigger is for example spring-loaded by any kind of spring mechanism on the inside of the vial gripper 28. Several key features are deemed necessary for convenient and reliable vial gripper 28 action: The preferred embodiment of a vial gripper 28 must allow an easy pick up of cryo-vials 10, it must hold on tight to a cryo-vial 10 during manipulation and it must be able to eject cryo-vials 10. These key features can be achieved by different trigger 48 positions. The trigger 48 positions can be held automatically by a built in latch mechanism or by a particular trigger 48 position achieved manually by a thumb. A chuck 49 is actually the very part of the vial gripper 28 that makes contact with the cryo-vial 10. The clamping surface of the chuck 49 corresponds with the inside diameter of a cryo-vial 10 cover which has the same dimension at the majority of currently used cryo-vials on the market. The chuck 49 is expanded and retracted by built-in spring mechanisms. An ejector pin 50 ensures that a cryo-vial 10 is reliably disengaged with the chuck 49 after retracting of the chuck 49.

To preserve the quality of thermolabile specimen it is absolutely necessary to maintain a cold temperature at all processing and storing steps. A preferred embodiment of a sample and tool holder 30 which is designed to support and accelerate most critical steps in storing at and retrieving specimen from a presented cryogenic storage and storage access system is shown in FIG. 7A. A sample and tool holder 30 consists of a platform 32 with an integrated cryo-vial box 31 cooled by liquid nitrogen. A handle 33 at the centre point of gravity is implemented for easy and convenient carrying of the sample and tool holder 30. A wireless barcode reader 34 may be attached to the sample and tool holder 30 in order to identify to be stored or retrieved receptacles 10 and to have this information directly transmitted to a control unit 35 controlling the light emitting guiding system 24. The sample and tool holder 30 may also include nests for tools 36 such as vial grippers 28, hooks 25 or forceps, pens, etc. The proposed sample and tool holder 30 can be either placed on a rim of a storage container 1 by means of a holder 56 as shown in FIG. 7B or be placed directly on top of a carrier structure 3.

A completely automatic storing and retrieval process can be achieved with an automatic version of the present invention as shown in FIG. 8A and FIG. 8B. However, several modifications to components of the automated storage and storage access system are necessary as compared to the manual setup. As an example a storage device 45 designed for an automatic operation might differ from a storage device 23 that is operated manually. At this storage device 45 individual elements 11 are rigidly connected with each other without hinges defining pivot points. The holding devices 62 are omitted to allow for insertion and removal of receptacles in a lateral direction 61.

According to the automated version of the present invention as shown in FIG. 8A, an insulating cover 38 may be rotatably mounted on a storage container 1 and may bear the complete automation machinery, which may consist of the following parts:

a vertical, thermally isolated tube 55 combined with a lifting mechanism 40 to lift a targeted storage device 45 in longitudinal direction 60 out of a storage container 1;

a cryo-vial handling device 52;

two actuators 37 and 39 to rotate the insulating cover 38 and to move the cryo-vial handling device 52 horizontally in a linear direction between the centre and the perimeter of the cover 38.

For storage and retrieval of samples, the insulating cover 38 features a narrow slot 54. As shown in FIG. 8B, the preferred embodiment of a cryo-vial handling device 52 may consist of a horizontal load and unload slide 46 to transfer cryo-vials 10 to and from a storage device 45 to a revolving nest 44 which is operated by a rotating mechanism 47 and located in an area cooled preferably by liquid nitrogen. To perform a storage or retrieval process, a motor 37 rotates the insulating cover 38 and a motor 39 moves a cryo-vial handling device 52 on a horizontal axis on the insulating cover 38 in order to bring the tube 55 to a correct rotational and radial position precisely above a targeted storage device 45. Pneumatic or electric actuators 41 are used to clamp the certain storage device 45, which is then lifted by a motor 40 in longitudinal direction 60 in respect to the carrier structure 3 out of the carrier structure 3 into the isolated tube 55 exactly to the very height so that the addressed storage position of a storage device 45 levels with the load and unload slide 46. After transfer of a receptacle 10 from the storage device 45 to the revolving nest 44 by a slide 46, the storage device 45 is driven back into the carrier structure 3. This process works for unloading receptacles 10 of the storage device 45 as well as vice versa for loading receptacles 10 to the storage device 45.

A barcode reader 42 installed next to the load and unload slide 46 may be used to unequivocally identify all cryo-vials 10 stored in or retrieved from the storage system. The revolving nest 44 is accessible for the operator through a lid 43 to remove automatically retrieved cryo-vials 10 or to insert them for automated storage.

For fast evacuation in case of malfunction of a storage container 1 an evacuation lid 48 in the insulating cover 38 is provided to be able to remove complete rack towers 51 from the storage container 1 and transfer them to another storage device.

The major benefits of this automated setup of the present invention beyond the advantages laid out above for the manual system are the complete lack of necessity to open a lid of the storage container 1 during normal operation, a constant remain of all receptacles 10 in a temperature-controlled environment during all storage and retrieval actions and an exclusion of mistakes by computer controlled processes and direct barcode identification of receptacles 10.

Although the present invention has been explained in relation to its preferred embodiments, it is to be understood that many other possible modifications and variations can be made without departing from the scope of the invention as hereinafter claimed.

LIST OF POSITION NUMBERS

| | |
|---|---|
| 1 | cryogenic storage container |
| 2 | insulating cover |
| 3 | carrier structure |
| 4 | intermediate platform |
| 5 | opening (of rack tower) |
| 6 | top surface (of rack tower) |
| 7 | shackle |
| 8 | rack marking |
| 9 | bottom holding device |
| 10 | receptacle, cryo-vial |
| 11 | element (middle element) |
| 12 | pivot point of elements |
| 13 | identification marking |
| 14 | small eye |
| 15 | top element |
| 16 | bottom element |
| 17 | top side of storage device |
| 18 | interior of storage container |
| 19 | corrugated metal sheet |
| 20 | pocket |

| | |
|---|---|
| 21 | rotary damper |
| 22 | gear rack |
| 23 | (manual) storage device |
| 24 | light-emitting guiding system |
| 25 | auxiliary tool |
| 26 | knob |
| 27 | (hook shaped) wire |
| 28 | vial gripper |
| 30 | sample and tool holder |
| 31 | integrated cryo-vial box |
| 32 | platform |
| 33 | handle |
| 34 | (wireless) barcode reader |
| 35 | control unit |
| 36 | tool |
| 37 | actuator (motor) |
| 38 | insulating cover |
| 39 | actuator (motor) |
| 40 | lifting mechanism (motor) |
| 41 | actuator (pneumatic/electric) |
| 42 | barcode reader |
| 43 | lid |
| 44 | revolving nest |
| 45 | (automatic) storage device |
| 46 | load and unload slide |
| 47 | rotating mechanism |
| 48 | evacuation lid |
| 49 | chuck |
| 50 | ejector pin |
| 51 | rack tower |
| 52 | handling device |
| 54 | narrow slot |
| 55 | isolated tube |
| 56 | holder |
| 57 | retaining mechanism |
| 58 | pivot angle |
| 59 | longitudinal axis |
| 60 | longitudinal direction (arrow) |
| 61 | lateral direction (arrow) |
| 62 | holding device |

The invention claimed is:

1. A storage device for storing receptacles in a carrier structure comprising:
a plurality of pockets each for holding an individual receptacle, wherein the pockets are connected one above the other in direction of a common longitudinal axis and the storage device being provided with openings for inserting and retrieving receptacles into and from said pockets in a longitudinal direction and/or in a lateral direction; and
a plurality of interconnected elements arranged one above the other, wherein each element comprises one of the plurality of pockets, wherein each of the plurality of elements is pivotably interconnected with its adjacent elements so that they are pivotable by a pivot angle in relation to the longitudinal axis.

2. The storage device according to claim 1, wherein each of the plurality of pockets is concentrically arranged with the longitudinal axis, and wherein a cross-sectional perimeter of each of the plurality of pockets is larger than a cross-sectional perimeter of the receptacle.

3. The storage device according to claim 1, wherein each of the plurality of pockets comprises at least one holding device preventing each receptacle from falling out of the storage device.

4. The storage device according to claim 1, wherein each of the plurality of pockets is accessible for insertion or removal of receptacles in the longitudinal direction from above when the upwardly adjacent element is pivoted from the longitudinal axis by the pivot angle.

5. The storage device according to claim 1, wherein each of the plurality of elements comprises a retaining mechanism securing neighbouring elements in dedicated positions, either in a rod-like position in a direction of the longitudinal axis or in a pivoted position hinged by the pivot angle.

6. The storage device according to claim 1, wherein each storage device and/or each of the plurality of pockets has an individual identification marking.

7. The storage device according to claim 1, wherein a top side of the storage device comprises an eye matching with a hook of an auxiliary tool.

8. A storage and storage-access system for storage of receptacles comprising:
at least one storage device according to claim 1;
a storage container having an interior and an open top;
a carrier structure mounted in the interior of the storage container providing a framework to store a plurality of storage devices in parallel in a vertical order, said carrier structure providing access openings on the top for enabling insertion and retrieval of storage devices in a vertical direction from above and, oppositely, a closed side at the bottom of the carrier structure to prevent the storage devices from falling out when the carrier structure is lifted.

9. The storage and storage-access system according to claim 8 further comprising:
a control unit for controlling the insertion and retrieval of receptacles from said storage and storage-access system; and
a light-emitting guiding system, operatively connected to the control unit, configured to project customized display markings onto the top surface of said carrier structure.

10. A method for manually storing or retrieving receptacles with a storage and storage-access system comprising:
providing the storage and storage-access system of claim 9;
generating an insertion order or retrieval order at the control unit of the storage and storage-access system to assign a specified storage position to a receptacle to be stored or retrieved;
identifying the specified storage position of the receptacle including a marking of a pocket of a targeted storage element in a storage device;
pulling out the identified storage device to the height of the targeted element;
pivoting the identified storage device;
placing said receptacle in the targeted pocket of said element in response to an insertion order, or
retrieving said receptacle out of the targeted pocket of said element in response to a retrieval order; and
sliding back said storage device into the carrier structure.

11. The method according to claim 10, further comprising scanning a marking or a barcode marking on the receptacle to identify the handled specimen in case of insertion into or removal from the storage system.

12. The method according to claim 10, further comprising identifying a rack marking of a targeted carrier structure by projecting an individual identification marking directly onto the top surface of the carrier structure by means of the light-emitting guiding system.

13. The storage and storage-access system according to claim 8 further comprising a barcode reader configured to identify markings of receptacles being inserted to or removed from said storage and storage-access system.

14. The storage and storage-access system according to claim 8 for cryogenic storage of cryo-vials, further comprising a cryogenic storage container with an insulating cover to recloseably cover the storage container wherein the top side of each storage device in a storage position within the carrier structure is plane with the top surface of the carrier structure.

15. The storage and storage-access system according to claim 14, further comprising a lifting mechanism to open and close the insulating cover, wherein the lifting mechanism is speed-controlled, the lifting mechanism comprising at least one rotary damper coupled with a gear rack.

16. The storage and storage-access system according to claim 8, wherein the receptacles comprise cryo-vials.

17. The storage device according to claim 1, wherein the receptacles comprise cryo-vials.

* * * * *